United States Patent [19]

Koes

[11] Patent Number: 5,308,744
[45] Date of Patent: May 3, 1994

[54] SOURCE OF PHOTOCHEMICALLY GENERATED ACIDS FROM DIAZONAPHTHOQUINONE SULFONATES OF NITROBENZYL DERIVATIVES

[75] Inventor: Thomas A. Koes, Riverside, Calif.
[73] Assignee: Morton International, Inc., Chicago, Ill.
[21] Appl. No.: 26,923
[22] Filed: Mar. 5, 1993
[51] Int. Cl.$^5$ .......................... G03F 7/23; G03F 7/30
[52] U.S. Cl. .................... 430/326; 430/165; 430/189; 430/192; 430/193; 430/270; 430/330; 534/557
[58] Field of Search ............ 430/192, 193, 189, 326, 430/330, 270, 165; 534/556, 557

[56] References Cited

U.S. PATENT DOCUMENTS

| | | | |
|---|---|---|---|
| 2,772,972 | 12/1956 | Herrick, Jr. et al. | 96/33 |
| 3,046,121 | 7/1962 | Schmidt | 96/33 |
| 4,421,844 | 12/1983 | Buhr et al. | 430/192 |
| 4,457,999 | 7/1984 | Stahlhofen | 430/189 |
| 4,467,025 | 8/1984 | Goto et al. | 430/191 |
| 4,491,628 | 1/1985 | Ito et al. | 430/270 |
| 4,632,900 | 12/1986 | Demmer et al. | 430/323 |
| 4,837,121 | 6/1989 | Blakeney et al. | 430/189 |
| 4,963,463 | 10/1990 | Koshiba et al. | 430/191 |
| 5,019,479 | 5/1991 | Oka et al. | 430/193 |

OTHER PUBLICATIONS

Tarascon et al., *Poly(t-BOC-styrene sulfone)-Based Chemically Amplified Resist for Deep-UV Lithography*, AT&T Bell Laboratories.
Frechet et al., *Polycarbonates Derived From o-Nitrobenzyl Clycidyl Ether: Synthesis and Radiation Sensitivity*, Dept. of Chemistry, Univ. of Ottawa, Ontario IBM Research Laboratory, San Jose, California.
Reichmanis et al., *The Effect of Substituents on the Photosensitivity of 2-Nitrobenzyl Ester Deep U.V. Resists*, J. Electrochem, Jun. 1983 (vol. 130, No. 6).
Reichmanis et al., *A Study of the Photochemical Response of o-Nitrobenzyl Cholate Derivatives in P(MMA-MAA) Matrices*, Journal of Polymer Science, Polymer Chemistry Edition, vol. 21, (1983).
Reichmanis et al., *o-Nitrobenzyl Photochemistry: Solution vs. Solid-State Behavior*, Journal of Polymer Science, Polymer Chemistry Edition, vol. 23 (1985)
Reichmanis et al., *A novel approach to -nitrobenzyl photochemistry for resists*, J. Vac. Sci. Technol., Nov/Dec. 1981.

Primary Examiner—Charles L. Bowers, Jr.
Assistant Examiner—John S. Chu
Attorney, Agent, or Firm—Robert M. Didrick; Gerald K. White

[57] ABSTRACT

A new photoacid generator having the formula

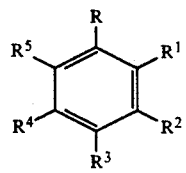

Formula I wherein
R = hydrogen, hydroxyl, or the —O—S(=O)$_2$—Q moiety;
R$^1$ = CH$_2$OS(=O)$_2$—Q, or —NO$_2$;
R$^2$ = CH$_2$OS(=O)$_2$—Q, or —NO$_2$;
R$^3$ = lower alkyl or hydrogen;
R$^4$ = hydrogen, —CH$_2$OS(=O)$_2$—Q, or —NO$_2$;
R$^5$ = hydrogen, —CH$_2$OS(=O)$_2$—Q, or —NO$_2$; and
Q is a diazonaphthoquinone moiety; with the proviso that R$^3$ is lower alkyl when R$^2$ and R$^4$ are NO$_2$, and with the proviso that R$^1 \neq$ R$^2$ and R$^4 \neq$ R$^5$.

exhibits unprecedented sensitivity to actinic radiation. This compound is photochemically transformed from a non-acidic entity to photoproducts which contain both sulfonic and carboxylic acid functuional groups. The acid generator is effective with polymers having acid labile groups, converting them into alkaline-soluble polymers, and with polymers which do not have such acid labile groups. Positive or negative working photoresist compositions containing the new photoacid generator have unparalleled performance characteristics because of the increased acidity generated per quantum of light.

A preferred photoacid generator is made by reacting 2,6-dimethylol-3,5-dinitro-p-alkyl phenol with a diazonaphthoquinone sulfonyl chloride.

12 Claims, 1 Drawing Sheet

SOURCE OF PHOTOCHEMICALLY GENERATED ACIDS FROM DIAZONAPHTHOQUINONE SULFONATES OF NITROBENZYL DERIVATIVES

FIELD OF THE INVENTION

This invention relates to a compound which forms an acid under the action of actinic radiation. More particularly, it relates to a compound which is capable of photochemical transformation from a non-acidic entity to photoproducts which contain both sulfonic and carboxylic acid functional groups. This acid-generating compound is particularly suitable in a positive working photoresist wherein portions exposed to patterned actinic radiation are rendered soluble in an aqueous alkaline developer while the unexposed portions remain intact to form an image of the pattern. It is also suitable in an image reversal photoresist composition wherein the acid-generating compound brings about an increased crosslink density leading to cure.

The sensitivity of photolithographic systems based on diazonaphthoquinone sensitized novolac resins is limited by both the quantum efficiency of the sensitizer to photoproduct conversion and the UV opacity of the novolac resins. Thus, the photoproduct conversion per photon of actinic radiation is generally too low for practical use in deep UV work because of the very low power that is available from exposure sources in those wavelengths. A dramatic increase in sensitivity in radiation-sensitive systems, often referred as chemical amplification, is obtained when a species produced in the primary photoreaction independently initiates a catalytic secondary reaction, thus increasing the quantum yield to values above one. For example, systems which photochemically produce a strong acid which then cleaves acid labile groups in a secondary reaction are disclosed in U.S. Pat. No. 3,915,706 for positive working polyaldehydes.

U.S. Pat. No. 5,037,721 teaches a positive radiation sensitive mixture that exhibits no change in the development time whether the time between irradiation and development is long or short and provides high structural resolution of the developed resist that is retained during processing steps subsequent to the development. Said mixture comprises a compound which forms an acid under the action of actinic radiation and a particular type of monomeric acid-cleavable compound which contains an acetal group. This patent has a good discussion of the acid-cleavable materials which have been employed and it is incorporated herein by reference.

U.S. Pat. No. 4,491,628 shows a deep UV sensitive resist composition which is made by combining a polymer having recurrent acid labile pendant groups, e.g., poly (p-tert-butoxycarbonyloxy-α-methylstyrene), with a cationic photo-initiator such as an aryldiazonium-, diaryliodonium-, or triarylsulfonium metal halide. Such compositions are taught there to be particularly useful and advantageous when used with deep UV light (200-300 nm) because they give very high resolution images with nearly vertical wall angles even in films thicker than 2 microns. Onium salts of Group VIa elements which have an $MF^-_6$ anion, exemplified by triarylsulfonium hexafluoroantimonate, are taught in U.S. Pat. No. 4,273,668 as cationic photoinitiators.

Such onium salts are not entirely satisfactory, however, because contamination of the silicon substrate of semiconductor chips by the heavy metal ions of said onium salts degrades the electrical properties of the chips. Also, the disposal of waste streams containing said metal ions is severely regulated. They are also quite complex to make and are very expensive.

Layers of positive working photoresists up to about 100μ thick and the resultant high aspect ratios are of increasing interest for a multitude of applications. For example, the electric conductance of magnetic head interconnection circuitry fabricated by the photoresist technique is increased by the increased thickness of the copper or other conductor which is plated on the substrate according to patterns outlined in the photoimaged and developed thick film resist. The film must have a uniform thickness and the sidewalls of the vias in the relief images developed therein must be substantially vertical. Currently, the typical thick film resists exhibit very poor thickness uniformity and are susceptible to outgassing and cracking when the thickness is greater than about 5μ.

Layers of positive working photoresists up to about 100μ thick and the resultant high aspect ratios are of increasing interest for a multitude of applications. For example, the electric conductance of magnetic head interconnection circuitry fabricated by the photoresist technique is increased by the increased thickness of the copper or other conductor which is plated on the substrate according to patterns outlined in the photoimaged and developed thick film resist. The film must have a uniform thickness and the sidewalls of the vias in the relief images developed therein must be substantially vertical. Currently, the typical thick film resists exhibit very poor thickness uniformity and are susceptible to outgassing and cracking when the thickness is greater than about 5μ.

There is, therefore, a need for a new and different photo acid generator (or PAG) which will chemically amplify the sensitivity of photoresist compositions. There is also a need for a different type of photoresist composition which can be applied to a substrate in one step to a thickness of up to 100 microns or more. Those needs have been met by the photo acid generator described herein which exhibits unprecedented sensitivity to actinic radiation. The increased activity per quantum of light renders positive or negative photoresist compositions having unparalleled performance characteristics.

SUMMARY OF THE INVENTION

It is an object of this invention to provide a new compound which will generate an acid upon radiolysis.

It is a related object of this invention to provide a new compound which will generate two types of acidity upon radiolysis.

It is another related object of this invention to provide a new compound which yields products upon radiolysis having a collective volume remarkably smaller than its original volume, thus leading to severe structural compromise in exposed areas of a networked film cast with this compound as an integral component.

It is another object of this invention to provide new, chemically amplified photoresist compositions.

It is a related object of this invention to provide recording materials comprising a >100 micron thick layer of the new photoresist composition.

It is yet another object of this invention to provide a method for producing an imaged recording material by actinic radiation of a photoresist composition chemically amplified by the new photo acid generator.

It is another object of this invention to provide a method for the preparation of the photoacid generator.

It is a further object of this invention to provide a novel compound which is an intermediate in the preparation of the photoacid generator.

It is a further object of this invention to provide a method for the preparation of the intermediate.

These and other objects which will become apparent from the following desription of the invention are achieved by a diazoquinone sulfonyl ester having the structure:

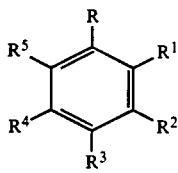

Formula I wherein
R = hydrogen, hydroxyl, or the —O—S(=O)$_2$—Q moiety;
R$^1$ = CH$_2$OS(=O)$_2$—Q, or —NO$_2$;
R$^2$ = CH$_2$OS(=O)$_2$—Q, or —NO$_2$;
R$^3$ = lower alkyl or hydrogen;
R$^4$ = hydrogen, —CH$_2$OS(=O)$_2$—Q, or —NO$_2$;
R$^5$ = hydrogen, —CH$_2$OS(=O)$_2$—Q, or —NO$_2$; and
Q is a diazonaphthoquinone moiety; with the proviso that R$^3$ is lower alkyl when R$^2$ and R$^4$ are NO$_2$, and with the proviso that R$^1 \neq$ R$^2$ and R$^4 \neq$ R$^5$.

DETAILED DESCRIPTION OF THE INVENTION

Figure 1:
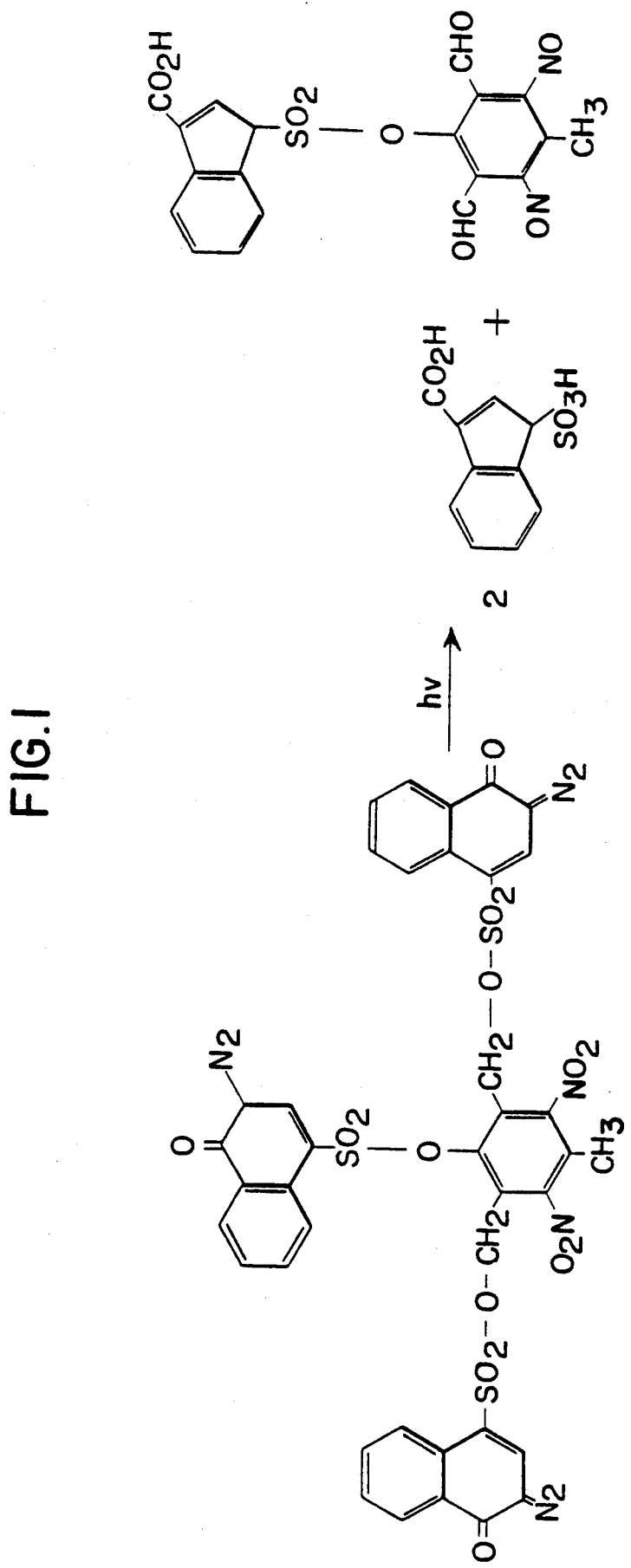

Preferred among the photo acid generators of this invention are those wherein R is —O—S(=O)$_2$—Q; R$^3$ is lower alkyl; R$^2$ and R$^4$ are nitro groups. R$^3$ is preferably a methyl group. Examples of PAG's of this invention include the tri-(2,1,4-diazonaphthoquinonesulfonate) ester of 3,5-dinitro-2,6-dimethylol para cresol and its 2,1,5-homolog. Both the 2,1,4- and 2,1,5-homologs are sometimes referred to hereinafter as the respective NMC triester. Other examples include the 2,1,4- and 2,1,5-diazonaphthoquinone sulfonate ester of 2-nitro benzyl alcohol.

Photo sensitive compositions of this invention having utility in g-line, i-line, and deep UV applications are made by combining a water-insoluble polymer or oligomer having having recurrent acid labile pendant groups with a PAG having the structure of Formula I. The composition is applied to a substrate, soft-baked under controlled conditions, exposed to actinic radiation by an imagewise protection, and post-baked under controlled conditions. The NMC triester, for example, yields both indene carboxylic acid and sulfonic acids when a photoresist containing it is irradiated at 365 nm, as shown in FIG. 1 of the drawing. In the areas of the applied film on which the radiation falls, the pendant acid labile groups are cleaved from the polymer backbone by the photo generated acids, leaving recurrent polar groups in their place so that the exposed areas are selectively removed by an alkaline developer or by a polar solvent. The unexposed portions of the film are non-polar and may be removed selectively, instead, by treatment with a non-polar solvent. Image reversal is possible, therefore, by selecting the developer and appropriate photoresist composition if a negative tone is desired.

The photo acid generator constitutes from about 5 to about 40% of the total weight of the photoresist of this invention. The more preferred amount is from about 5 to about 15%.

The polymers and oligomers of this invention include vinylic polymers with or without pendant acid labile groups that produce acidolysis products that differ significantly in polarity, i.e., solubility, from that of their precursors. Polymers of hydroxystyrene and copolymers thereof with styrene, vinyl chloride, methyl vinyl ether, acrylonitrile, and an acrylic or methacrylic acid ester such as methylmethacrylate are examples of vinylic polymers that may serve as backbone polymers for acid labile polymers useful in this invention. The backbone polymers may be present along with their acid labile derivatives. Partial esterification of the hydroxyl groups by acetic anhydride and the like is also contemplated. Condensation polymers and oligomers may also serve as the backbone of acid labile resins useful in this invention, alone or in combination with the vinylic polymers. The preferred acid labile groups pendant from those backbones are tert-butyl esters of carboxylic acids and tert-butylcarbonates of phenols but other groups such as trityl, benzyl, benzhydryl, and other well known acid labile groups are also operative in this invention. Polymers and oligomers useful in this invention include poly-(p-tert-butoxycarbonyloxy-α-methylstyrene), poly-tert-butyl-p-vinylbenzoate, poly-(tert-butoxycarbonyloxystyrene/methylmethacrylate) and others disclosed in the aforementioned U.S. Pat. No. 4,491,628, which is incorporated herein by reference. The t-butoxycarbonyloxy group will sometimes be referred to hereinafter as the t-Boc group.

Thus, for example, a photosensitive composition of this invention may include acrylate resins of varying acidity and molecular weight which have utility in primary imaged, broadband i-line exposure applications whether developed in metallic or non-metallic alkaline developer solutions of varying concentrations.

Photosensitive compositions whose unexposed dissolution inhibition characteristics are not enhanced by chemically protecting copolymers from aqueous alkaline development through the use of acid labile groups but rather by increasing the non-polar content of the copolymer also exemplify the invention. The ratio of hydroxystyrene and styrene in a copolymer, for example, may be adjusted to afford an optimum balance between dissolution inhibition of unexposed areas and susceptibility to aqueous alkaline development of the exposed areas. Shrinkage of the photoresist in the exposed areas due to the smaller volume of the photoproducts from the photoacid generator of this invention leads to a structural breakdown of the exposed photoresist. The generated acids and the hydroxyl-containing copolymers are dissolved by the alkaline developer.

The optimal level of esterification with the t-Boc group depends in part on the nature of the backbone polymer. For example, in the case of hydroxystyrene/methylmethacrylate copolymers, the optimal level is from about 10 to about 60 percent by weight whereas the optimal level for a hydroxystyrene/styrene copolymer is from about 1 to about 35 percent.

Other resins such as the 2-diazo-1-naphthoquinone-4-sulfonyl ester of a novolac resin from the condensation of cresol and formalddehyde and its 2,1,5-homolog may be included in the photoresist compositions of this invention. If present, the amount may be from about 20 to about 35 percent by weight of solids in the total composition.

Additives such as surfactants, anti-oxidants, pigments, dyes, sensitizers, and de-foaming agents may be incorporated into the photoresist compositions of this invention. Organic solvents are used to adjust the viscosity of the photoresist composition and facilitate the application of the photoresist to the substrate by spin coating, flow coating, row coating, or any other conventional method. Examples of the solvents include ethyl lactate, glycol ethers, such as mono- and di-alkyl ethers of ethylene and diethylene glycol ethylene glycol, acetates and other lower carboxylic acid esters of the monoalkyl ethers, aromatic hydrocarbons, ketones, and the like. The concentration of the photoresist composition in the solution may be from about 25 to about 70% by weight.

A photoresist coating may be applied to a silicon wafer by first depositing hexamethyldisilazane as an adhesion promoter on the wafer and spreading it out evenly by spinning the wafer at 2000 rpm for 5 seconds and then at 5000 rpm for 15 seconds. The photoresist may then be spread evenly over the wafer by spinning the coated wafer in like manner. Coatings may also be drawn down with a doctor blade. The appropriate wet thickness is applied, allowing for loss of solvent and film thickness upon baking.

The invention is illustrated in more detail by way of the following examples wherein all parts and percentages are by weight unless otherwise stated.

Preparation of 3,5-dinitro-2,6-dimethylol-p-cresol

To 67.2 parts (0.4 mole) of 2,6-dimethylol-p-cresol (PMC Specialties Group, PMC, Inc., Cincinnati) in 1500 parts of deionized water in a reaction vessel there was added 100 parts of a 70.7% aqueous solution of nitric acid (1.12 moles) over a period of 5 minutes with vigorous stirring at room temperature. The reaction mixture was stirred vigorously at room temperature for 8 hours and then was quiescent for about 16 hours before being stirred again for 2 hours. The mixture was then filtered through a Büchner funnel with the aid of a vacuum. The wetcake was washed with deionized water until a pH of the filtrate was about 4 to 5 and then it was dried in a vacuum dessicator at room temperature. The yield was 74 parts which is 71.2% of the theoretical yield.

EXAMPLE 1

The tri-(2,1,4-diazonaphthoquinonesulfonate) ester of 3,5-dinitro-2,6-dimethylol para cresol (i.e., 214 NMC triester) was made by adding 4.22 parts (0.016 equivalent) of 2,1,4-diazonaphthoquinone sulfonyl chloride to 1.35 parts (0.0052 equivalent) of 3,5-dinitro-2,6-dimethylol para cresol and lowering the temperature to 0° C. Then a solution of 1.60 parts of triethylamine in 70.4 parts of propyleneglycol monomethyl ether was added to the mixture while maintaining the temperature within the range of 0° to about 10° C. The esterification was allowed to proceed in this temperature range for 4 hours and the reaction mixture was added to de-ionized water acidified with hydrochloric acid while vigorously stirring the water. The product precipitated from the water and was separated on a Büchner funnel by vacuum filtration. Water washing and vacuum drying of the filter cake gave 4.90 parts (98%) of the desired product. A $C_{13}$ NMR analysis of the product showed that essentially all of the diazo chloride had reacted.

EXAMPLE 2

A photoresist composition was made by homogenizing a mixture of 4.0 parts of a t-butylcarbonyloxy ester of a hydroxy styrene/styrene (70/30 by weight) in which 28% by weight of the available hydroxyl groups were esterified, 1.0 part of the product of Example 1, and 7.6 parts of ethyl lactate. The resist was drawn down on a copper clad epoxy laminate and baked at 100° C. for 5 minutes to give a 1.1 mil (28 micron) thick coating. The coating was exposed at 20 mJ/cm$^2$ on an ORC-HMW broad band i-line exposure unit generally used in the PCB industry for primary imaging of negative tone laminated dry-film photoresists. No post-exposure bake was used before the coating was developed for 8 minutes at room temperature in a 1.5% aqueous solution of sodium hydroxide. Etching of the imaged resist with CuCl$_2$ gave 2 mil lines and spaces clear to the substrate

EXAMPLE 3

Several copper clad epoxy laminates were coated with a photoresist containing 29.18% of a hydroxystyrene resin (MW=13500) having 40% of its hydroxyl groups acetylated, 9.69% of a 48% t-Boc esterified hydroxystyrene/styrene (70/30) copolymer having a MW of 4000-6000, 10.61% of the NMC triester, and 50.52% of ethyl lactate. The solids content was 49.5% and the viscosity of the solution was 1500-1600 cps at 25° C. On a solids basis, the acetylated resin constituted 59%, the t-Boc ester 19.6%, and the NMC triester 21.4% of the total. Coat thicknesses in the 1 to 2 mil range were achieved after soft baking at 80° C. for 10 minutes. Coated panels were exposed to patterned actinic radiation consisting of a broad band of frequencies with the i-line, 365 nm, being the major component at energies of from 58 to 166 mJ/cm$^2$ and baked at 80° C. for 5 minutes. Development of these coated panels in DE-3 gave images which were shown by optical microscope inspection to have side wall angles of vertical integrity. Acid etching of a panel with a 3N cupric chloride solution at 120° F. at a track speed of 35"/minute left the resist lines unharmed.

EXAMPLE 4

Coatings in excess of 100 microns were achieved with a resist containing 66% solids but otherwise similar to the composition of Example 3. The resist exhibited excellent photospeed (i.e., 30-100 mJ/cm$^2$) at 365 nm, no inhibition layer, and low film loss during development with non-metallic aqueous alkaline developer.

EXAMPLE 5

A photoresist composition containing 18.86 parts of a hydroxystyrene/methylmethacrylate resin in which 35% of the hydroxyl groups are t-Boc esterified, 5.14 parts of NMC triester, 0.01 part of FC 430 flow agent, and 76 parts of ethyl lactate was applied to wafers of silicon and soft baked to give a coating having a 1.0 micron thickness. The coated wafer was then exposed to patterned irradiation at 254 nm and 70-80 mJ/cm$^2$. One wafer was developed by a two puddle process using 2.38% NMD-3 with a 2 second spray, a 3 second spray, and a 25 second puddle so that the total developing time was 60 seconds. Another wafer was developed in similar fashion except that each puddle step was 40 seconds so that the total time was 90 seconds. Although the photospeed was somewhat slow, the images had vertical profiles in each instance.

EXAMPLE 6

Several copper clad epoxy laminates were coated with a photoresist containing 3.9% of an acrylate resin having a molecular weight of 90,000 and an acid number of 130.3 (sold under the trademark RMB 610), 32.5% of an acrylate resin having a molecular weight of 20,000 and an acid number of 238.8 (sold under the trademark RMB 680), 3.9% of the 2.25 functional 2,1,5-diazonaphthoquinone sulfonate ester of 3,5-dinitro-2,6-dimethylol para cresol and 59.6% of methyl ethyl ketone. The solids content was 40.3% and the viscosity of the solution was about 1000 cps at 25° C. On a solids basis, the acrylate resins were 90% and the PAG was 10%. The weighted average for the molecular weight and acid number of the 9:1 mixture of the two acrylate resins was 27000 and 228, respectively. The monomer mixture for the RMB 610 resin was: 20% methyl methacrylate, 10% ethyl acrylate, 50% styrene, and 20% methacrylic acid. The monomer mixture for the RMB 680 resin was 69.7% styrene and 30.3% acrylic acid. Coated thicknesses in the 0.5 mil to 0.7 mil range were achieved upon soft baking at 100° C. for 5 minutes. The coated panels were then exposed to pattened actinic radiation having a frequency of 365 nm as the major component of a broad based light siurce at energies ranging from 28 to 84 mJ/cm². No post exposure bake was required. Development of the panels was carried out using a Höllmüller automated conveyor system, and a 1% aqueous sodium carbonate developer at 85° F. and conveyor speeds ranging from 2.8 to 3.4 ft/min. Optical microscope inspection indicated that 0.6 mil (about 15 micron) lines and spaces were resolved when the exposure energy was 80 mJ/cm² and the conveyor speed was 3 ft/min.

EXAMPLE 7

Copper clad epoxy laminates were coated with a photoresist containing 13.3% of a hydroxystyrene/styrene (70/30) copolymer having a molecular weight in the range of from 2500 to 4000 daltons (Maruzen CST 70), 13.3% of a hydroxystyrene/styrene (50/50) copolymer having a molecular weight in the range of from 3000 to 5000 daltons (Maruzen CST 50), 6.7% of a 214 NMC ester in which 2.25 of the possible 3 sulfonate groups are present, and 66.7% of ethyl lactate. A coated thickness of 0.6 mil on 1 ounce copper clad epoxy was achieved upon a soft bake of 100° C. for 5 minutes. Exposure: 28 mJ/cm² using an ORC-HRW broad band imaging unit. Development was carried out by immersion for 90 seconds in an agitated 1.3% aqueous sodium hydroxide solution at 22° C. Good linearity between the artwork and the imaged resist was achieved as was resolution of 1 mil lines and spaces.

EXAMPLE 8

The preparation of the 2,1,4-diazonaphthoquinone sulfonyl ester of 2-nitrobenzyl alcohol was carried out according to the general procedure of Example 1 except for the substitution of an amount of 2-nitrobenzyl alcohol equivalent to the amount of 2,1,4-diazonaphthoquinone.

EXAMPLE 9

A photosensitive resist composition containing 16.12% of a novolac resin (m-, p-cresol/formaldehyde; mol. wt.: 5000 daltons); 3.02% of the t-Boc ester of pyrogallol (95% esterified), 3.69% of the product of Example 8, 0.05% of Troykyd 366 film forming agent, and 77.12% of propylene glycol monomethyl ether acetate was spin coated onto silicon wafers to give a 1 micron thick film when dried. The coated wafers were then irradiated with patterned deep UV light, post-exposure baked, and developed in aqueous tetramethyl ammonium hydroxide (NMD-3) to give images having good sidewall profiles. In some cases, the post-exposure bake was delayed for 3 hours while the irradiated resist was subjected to hexamethyldisilazane (HMDS) vapors. Latent image decay was not observed.

The subject matter claimed is:

1. A diazoquinone sulfonyl ester having the structure:

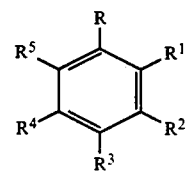

Formula I wherein
R = hydrogen, hydroxyl, or the $-O-S(=O)_2-Q$ moiety;
$R^1 = CH_2OS(=O)_2-Q$, or $-NO_2$;
$R^2 = CH_2OS(=O)_2-Q$, or $-NO_2$;
$R^3 =$ lower alkyl or hydrogen;
$R^4 =$ hydrogen, $-CH_2OS(=O)_2-Q$, or $-NO_2$;
$R^5 =$ hydrogen, $-CH_2OS(=O)_2-Q$, or $-NO_2$; and
Q is a diazonaphthoquinone moiety; with the proviso that $R^3$ is lower alkyl when $R^2$ and $R^4$ are $NO_2$, and with the proviso that $R^1 \neq R^2$ and $R^4 \neq R^5$.

2. The diazoquinone sulfonyl ester of claim 1 wherein R, $R^3$, $R^4$, and $R^5$ are hydrogen; $R^1$ is $-CH_2OS(=O)_2-Q$, and $R^2$ is $-NO_2$.

3. The diazoquinone sulfonyl ester of claim 1 wherein R is $-O-S(=O)_2-Q$; $R^3$ is lower alkyl; $R^2$ and $R^4$ are $-NO_2$; and $R^1$ and $R^5$ are $-CH_2-O-S(=O)_2-Q$.

4. The ester of claim 3 wherein $R^3$ is methyl.

5. The ester of claim 2 wherein the sulfonyl group is attached to the diazonaphthoquinone moiety at the 4 position.

6. The ester of claim 2 wherein the sulfonyl group is attached to the diazonaphthoquinone moiety at the 5 position.

7. A photo acid generator having the structure:

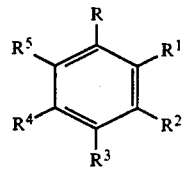

Formula I wherein
R = hydrogen, hydroxyl, or the $-O-S(=O)_2-Q$ moiety;
$R^1 = CH_2OS(=O)_2-Q$, or $-NO_2$;
$R^2 = CH_2OS(=O)_2-Q$, or $-NO_2$;
$R^3 =$ lower alkyl or hydrogen;
$R^4 =$ hydrogen, $-CH_2OS(=O)_2-Q$, or $-NO_2$;
$R^5 =$ hydrogen, $-CH_2OS(=O)_2-Q$, or $-NO_2$; and Q is a diazonaphthoquinone moiety; with the proviso that R³ is lower alkyl when R² and R⁴ are NO₂, and with the proviso that R¹≠R² and R⁴≠R⁵.

8. The photo acid generator of claim 7 wherein R is —O—S(=O)₂—Q; R³ is lower alkyl; R² and R⁴ are —NO₂; R¹ and R⁵ are —CH₂O—S(=O)₂—Q.

9. A method for the preparation of relief structures on a semiconductor substrate which comprises coating the substrate, with, a positive working photoresist composition comprising, in admixture, a water-insoluble polymer having an acid-cleavable moiety in its structure which inhibits solubility of the polymer in an aqueous alkaline medium, and the photo acid generator of claim 7, drying the composition, exposing it imagewise to actinic radiation; baking the exposed photoresist coating; and applying an aqueous alkaline developer to the exposed coating.

10. The method of claim 9 wherein R³ is methyl.

11. A method for the preparation of the compound of claim 3 comprising adding a diazonaphthoquinone sulfonyl chloride to a compound having the formula:

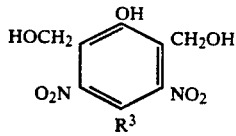

and adding a hydrogen chloride scavenger and a non-aqueous polar solvent to the mixture.

12. The photo acid generator of claim 7 wherein R¹ and R⁵ are —CH₂O—S(=O)₂—Q and R² and R⁴ are —NO₂.

* * * * *